(12) United States Patent
Taniguchi

(10) Patent No.: US 8,471,693 B2
(45) Date of Patent: Jun. 25, 2013

(54) DEGRADATION AND METALLIC SALT SENSING FOR BIOMASS FUEL

(75) Inventor: Satoshi Taniguchi, Numazu (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/060,139

(22) PCT Filed: Oct. 28, 2009

(86) PCT No.: PCT/JP2009/068496
§ 371 (c)(1),
(2), (4) Date: Feb. 22, 2011

(87) PCT Pub. No.: WO2011/052052
PCT Pub. Date: May 5, 2011

(65) Prior Publication Data
US 2012/0206253 A1    Aug. 16, 2012

(51) Int. Cl.
*G08B 21/00* (2006.01)
(52) U.S. Cl.
USPC ............. 340/438; 340/439; 73/53.01; 436/60
(58) Field of Classification Search
USPC ..... 340/438, 439; 701/101; 436/60; 73/53.01
See application file for complete search history.

(56) References Cited

U.S. PATENT DOCUMENTS

| 8,202,730 B2 * | 6/2012 | Cummings | 436/60 |
| 2010/0020325 A1 * | 1/2010 | Osaki et al. | 356/436 |
| 2010/0211289 A1 * | 8/2010 | Yoshida et al. | 701/103 |

FOREIGN PATENT DOCUMENTS

| JP | A-2007-146674 | 6/2007 |
| JP | A-2008-281486 | 11/2008 |
| JP | A-2009-2887 | 1/2009 |
| JP | A-2009-13884 | 1/2009 |
| JP | A-2009-79978 | 4/2009 |
| JP | A-2009-167853 | 7/2009 |

OTHER PUBLICATIONS

International Search Report mailed Feb. 2, 2010 issued in International Patent Application No. PCT/JP2009/068496 (with translation).

* cited by examiner

*Primary Examiner* — Jeffery Hofsass
(74) *Attorney, Agent, or Firm* — Oliff & Berridge, PLC

(57) ABSTRACT

When biomass fuel reacts with oxygen for a long period of time, an amount of acid ions in a tank is increased with time. However, when metallic ions are generated for some reason and the reaction proceeds to change the acid ions into metallic salts, the increase rate of the amount of the acid ions in the fuel tank becomes slow. When the metallic salt forming reaction proceeds rapidly, the amount of the acid ions may even be reduced. Therefore, in the embodiment, the change of the acid ions into the metallic salts in a fuel is detected. Unless the fuel is newly supplied by refueling, the decrease of the amount of acid ions in the fuel can be considered as a change into metallic salts. Accordingly, the generation of metallic salts can be detected by monitoring the decrease of the amount of acid ions in the fuel. Thus, clogging of a fuel supply system or the like caused by the metallic salt forming reaction can be prevented.

4 Claims, 4 Drawing Sheets (A)

(B)

DEGRADATION AND METALLIC SALT SENSING FOR BIOMASS FUEL

TECHNICAL FIELD

The present invention relates to a fuel degradation detector for an internal combustion engine. More particularly, the present invention relates to a fuel degradation detector for an internal combustion engine capable of detecting a degree of oxidative degradation of biomass fuel.

BACKGROUND ART

For example, Patent Literature 1 discloses a fuel degradation detector including: detecting means for detecting a degree of oxidative degradation of biomass fuel derived from vegetable materials such as sugar cane, corn, palm oil, rapeseed, coconut, and soybean; and warning means for warning a driver when the detected degree of oxidative degradation exceeds a threshold. A fatty acid ester biomass fuel may release an acid by reaction with oxygen in air. The released acid causes metallic corrosion or the like of engine parts of a vehicle. Therefore, the device disclosed in Patent Literature 1 measures an acid value in a fuel tank and turns on a warning light when the measured acid value exceeds a threshold, thereby enabling a driver to be informed that some countermeasures should be taken before the metallic corrosion or the like of the engine parts is caused.

CITATION LIST

Patent Literature

Patent Literature 1: Japanese Patent Laid-Open No. 2008-281486
Patent Literature 2: Japanese Patent Laid-Open No. 2009-167853
Patent Literature 3: Japanese Patent Laid-Open No. 2009-079978

SUMMARY OF INVENTION

Technical Problem

A free acid is considered to exist in biomass fuel in an ionic state. Therefore, metallic corrosion or the like can be prevented by monitoring an ion amount of free acid, as is disclosed in Patent Literature 1. However, a free acid may change into a metallic salt when combined with a metallic ion. When a free acid changes into a metallic salt, clogging of a fuel supply system such as a filter, deposits or the like may be caused. When the free acid changes into the metallic salt rapidly, such problems may become more salient. Accordingly, when a free acid changes into a metallic salt, clogging of the fuel supply system, deterioration of fuel efficiency and deterioration of the emission may be caused even though the ion amount of the free acid is less than a threshold.

The present invention is made to solve such problems, and seeks to provide a fuel degradation detector for an internal combustion engine capable of detecting the generation of a metallic salt derived from biomass fuel.

Means for Solving the Problem

To achieve the above mentioned purpose, a first aspect of the present invention is a fuel degradation detector for an internal combustion engine, comprising:
fuel supplying means for supplying biomass fuel to the internal combustion engine;
degradation index obtaining means for regularly obtaining a degradation index indicating a degree of oxidative degradation of the biomass fuel stored in the fuel supplying means;
decrease ratio obtaining means for obtaining a decrease ratio of the regularly obtained degradation index during a predetermined set period;
decrease ratio determining means for determining that a metallic salt derived from the biomass fuel has increased in amount when the decrease ratio is higher than a predetermined first threshold; and
warning means for warning a driver when it is determined that the biomass fuel has degraded or the metallic salt has increased in amount.

A second aspect of the present invention is the fuel degradation detector for an internal combustion engine according to the first aspect, further comprising:
degradation index determining means for determining that the biomass fuel has degraded when the degradation index is higher than a predetermined second threshold,
wherein the decrease ratio obtaining means obtains the decrease ratio when the degradation index is lower than the second threshold.

Advantageous Effects of Invention

In accordance with the first aspect of the present invention, it can be determined that a metallic salt derived from biomass fuel is increased in amount when a decrease ratio is higher than a predetermined first threshold. Thus, clogging of a fuel supply system, deterioration of fuel efficiency, and deterioration of the emission along with the rapid increase of the amount of the metallic salt can be prevented.

In accordance with the second aspect of the present invention, a decrease ratio during a set period of a degradation index can be obtained when the degradation index is lower than a second threshold. Thus, the problems of clogging of the fuel supply system, deterioration of fuel efficiency, and deterioration of the emission which are caused even when an ion amount of a free acid is smaller than a threshold can be reliably avoided.

Figure 1:
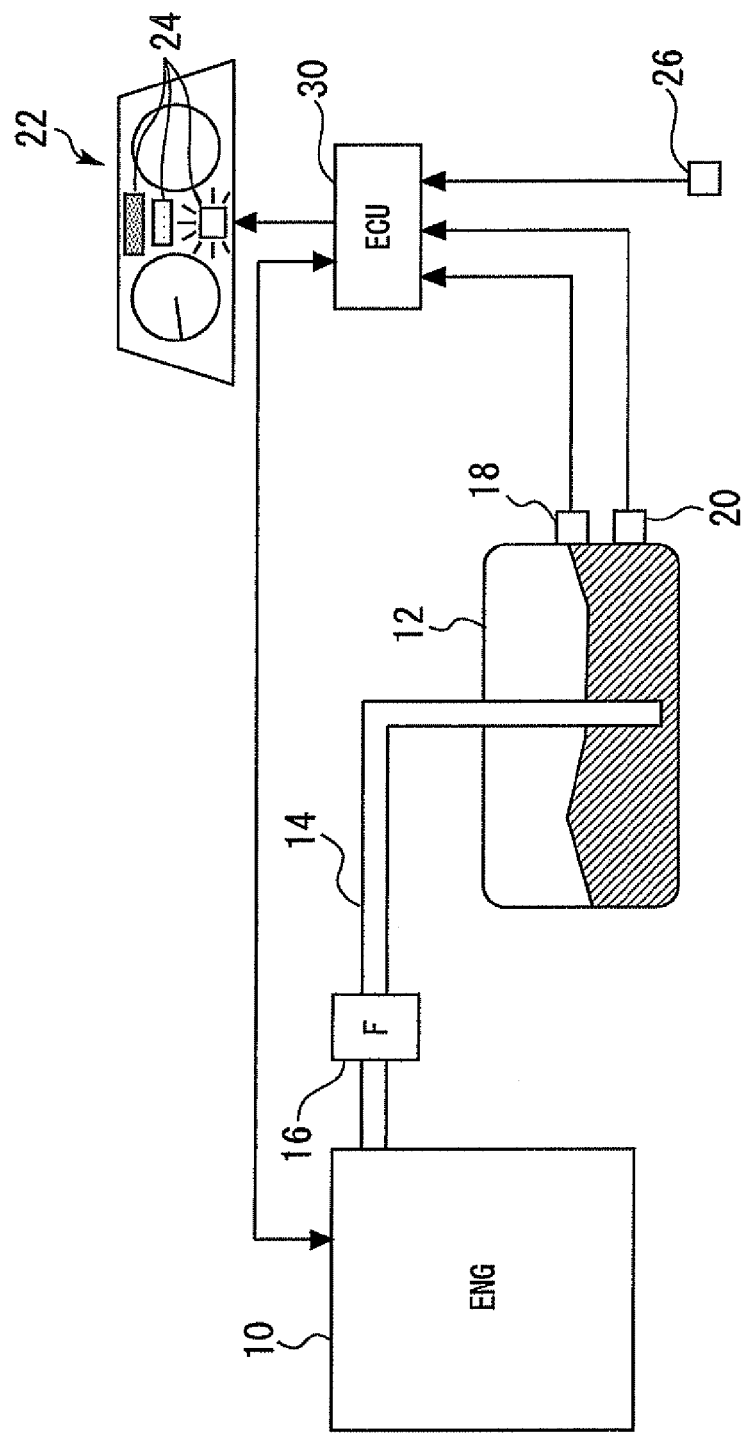
FIG. 1 is an illustration for describing a system configuration according to a first embodiment of the present invention.

DESCRIPTION OF REFERENCE NUMERALS 10 diesel engine
12 fuel tank
14 fuel pipe
18 dielectric constant sensor
20 level sensor
22 instrument panel
24 display

BEST MODE FOR CARRYING OUT THE INVENTION

First Embodiment

[Description of System Configuration]
FIG. 1 is an illustration for describing a system configuration according to a first embodiment of the present invention.

The system shown in FIG. 1 includes a diesel engine 10 mounted on a vehicle. Fuel in the diesel engine 10 is stored in a fuel tank 12. A mixed fuel of light oil and biomass fuel is supplied to the fuel tank 12.

The fuel in the fuel tank 12 is delivered to the diesel engine 10 through a fuel pipe 14. A fuel filter 16 is provided on the fuel pipe 14. Fuel delivered through the fuel filter 16 is pressurized by a fuel pump (not shown), stored in a common rail (not shown) in a highly pressurized state, and distributed to a fuel injection valve (not shown) of each cylinder from the common rail.

A dielectric constant sensor 18 capable of detecting an amount of ions of a free acid (hereinafter referred to as "acid ions") in the fuel tank 12 is provided on the fuel tank 12. The dielectric constant sensor 18 is not limited to be provided on the fuel tank 12. For example, the dielectric constant sensor 18 may be provided on a fuel supply path such as the fuel pipe 14. A level sensor 20 capable of detecting a liquid level of the fuel tank 12 is further provided on the fuel tank 12.

An instrument panel 22 of the vehicle on which the diesel engine 10 is mounted includes a display (warning light) 24 for informing a driver of a current situation or a need of oil change when it is determined that an amount of acid ions exceeds an allowable value or when it is determined that the amount of acid ions has been continuously reduced.

The system according to the embodiment further includes an ECU (Electronic Control Unit) 30. The ECU 30 is connected to the above-described dielectric constant sensor 18, the level sensor 20, an opening/closing sensor 26 of a fuel lid, and various sensors for detecting an operating state of the diesel engine 10. Also, the ECU 30 is connected to various actuators for controlling the operating state of the diesel engine 10. Furthermore, various kinds of actuators for controlling the operating state of the diesel engine 10 are connected to the ECU 30. The ECU 30 is further connected to the display 24.

Figure 2:
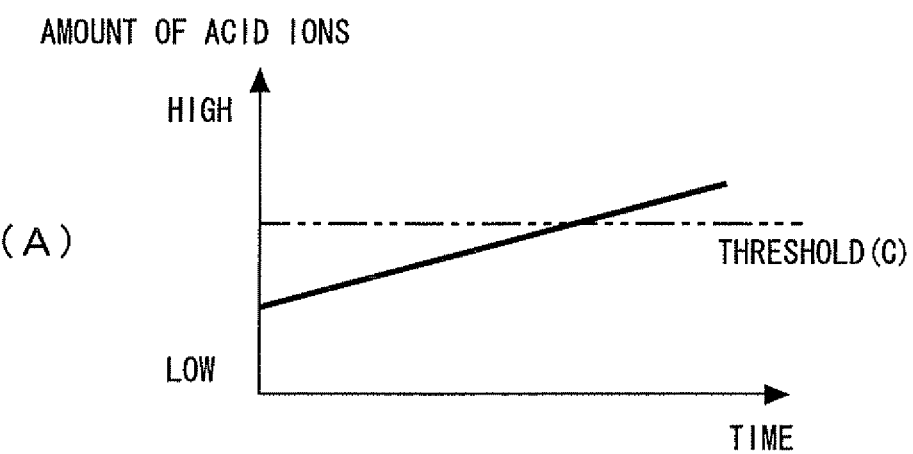
FIG. 2 is a graph showing a temporal change of an amount of acid ions.
Figure 2:
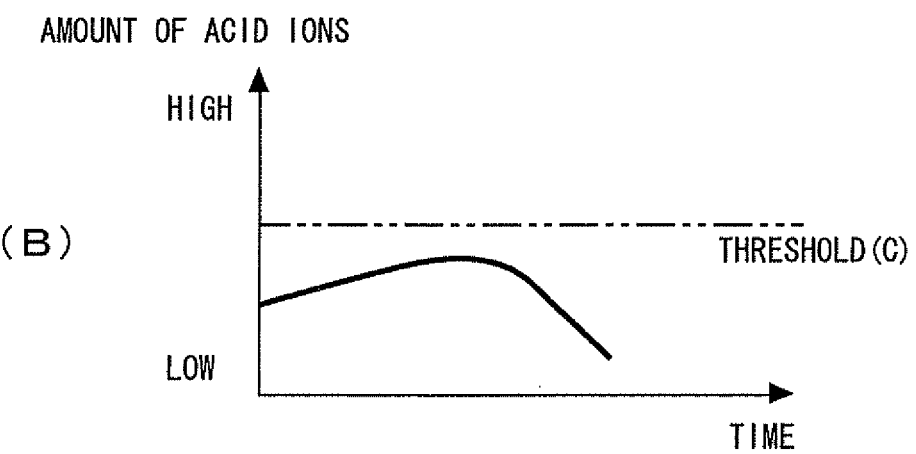

A fatty acid ester biomass fuel such as a fatty acid methyl ester has poor oxidative stability due to its structure having a double bond. Therefore, when such a biomass fuel is used, the generation of acid ions as a barometer of a degree of oxidation needs to be considered. The amount of generated acid ions in the biomass fuel will be described referring to FIG. 2(A). In general, the reaction of biomass fuel with oxygen proceeds with the passage of time. For example, when the vehicle is not driven for a long period of time or when refueling is not done for a long period of time, the biomass fuel is stored in the fuel tank 12 for a long period of time. Under such a circumstance, the biomass fuel reacts with oxygen over a long period of time and the amount of acid ions in the fuel tank 12 increases with time as shown in FIG. 2(A).

The acid ions cause metallic corrosion or the like of engine parts of the vehicle. Accordingly, a limit value (C) as shown in FIG. 2(A) is obtained through experiment or the like in advance. When the amount of the acid ions in the fuel tank 12 exceeds the limit value (C) shown in FIG. 2(A), the display 24 displays a warning for a driver. Thus, a fuel containing acid ions is prevented from being supplied to the diesel engine 10 and therefore metallic corrosion or the like can be avoided.

However, the present inventor has focused their attention on the fact that monitoring the increase of the amount of the acid ions in the fuel is not sufficient. The fuel supply system of the diesel engine 10 is made of various metallic materials. Accordingly, when the metallic materials are ionized for some reason, they may be combined with acid ions. When metallic ions are combined with acid ions, the acid ions change into metallic salts. The metallic salts may cause clogging of a fuel supply system such as a filter, deposits or the like. Therefore, when acid ions which have changed into metallic salts exist in the fuel, clogging of the fuel supply system or the like may be caused even though the amount of acid ions in the fuel is small.

The above-described phenomenon will be explained referring to FIG. 2(B) in detail. When biomass fuel reacts with oxygen for a long period of time, the amount of acid ions in the fuel tank 12 is increased with time. However, when metallic ions are generated for some reason and the reaction proceeds to change the acid ions into metallic salts, the increase rate of the amount of the acid ions in the fuel tank 12 becomes slow. When the metallic salt forming reaction rapidly proceeds, the amount of acid ions may even be reduced. Even in such a circumstance, a warning for a driver is not displayed when the amount of acid ions is smaller than the limit value (C). Therefore, some other countermeasures besides monitoring the increase of the amount of the acid ions in the fuel are required.

In the embodiment, the change of acid ions into metallic salts in the fuel is detected. Unless fuel is newly supplied by refueling, a decrease of the acid ions in the fuel can be considered as a change into metallic salts. Accordingly, the generation of metallic salts can be detected by monitoring the decrease of the amount of acid ions in the fuel. Thus, clogging of the fuel supply system or the like caused by the metallic salt forming reaction can be prevented.

Figure 3:
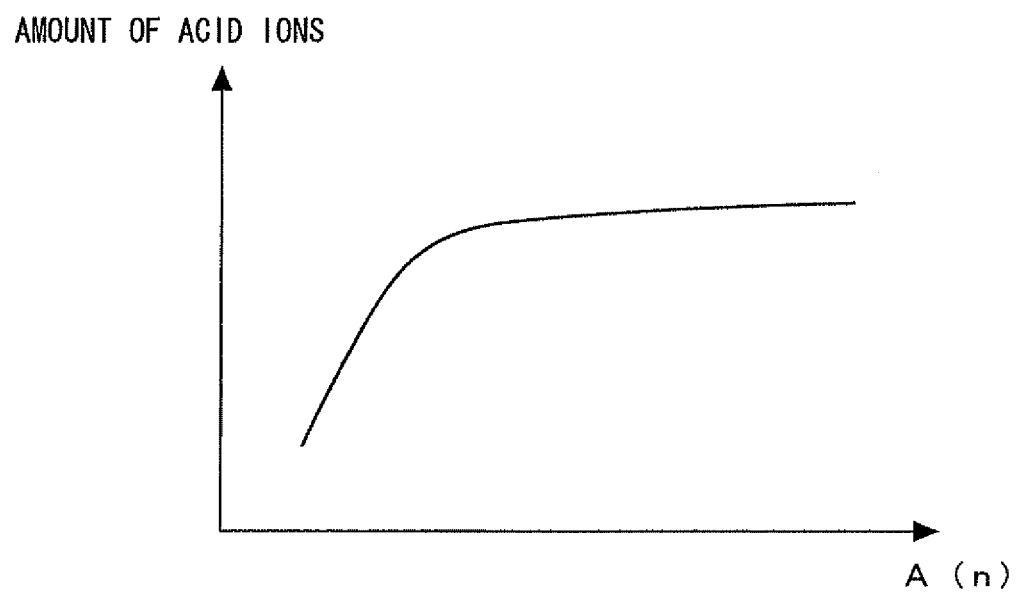
FIG. 3 is an example of a map showing a relation between a dielectric constant and an amount of the acid ions.

The amount of acid ions in the fuel can be obtained by the output of the dielectric constant sensor 18. The metallic salts in the fuel have smaller electrical characteristics compared to their ionic states and therefore have an extremely small impact on the sensor output. Thus, the amount of the acid ions in the fuel can be estimated by obtaining the output of the dielectric constant sensor 18. A characteristics map indicating a relation between the amount of acid ions in the fuel and the output of the dielectric constant sensor 18 is stored in the ECU 30. FIG. 3 shows one example of such a characteristics map. The characteristics map can be prepared through experiment or the like.

[Specific Process in First Embodiment]

Figure 4:
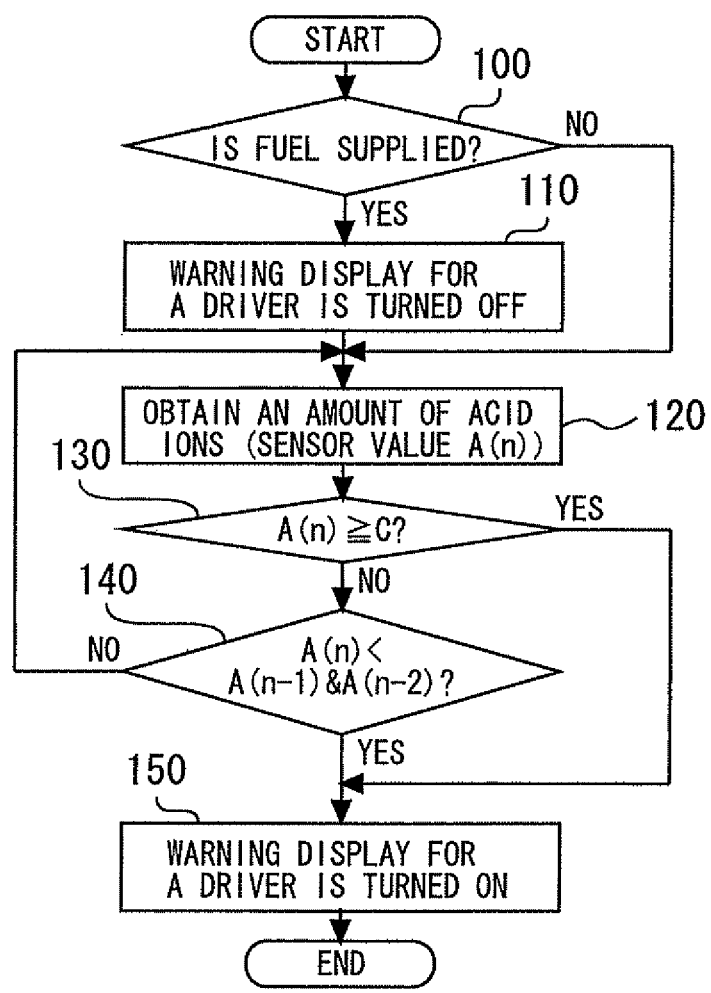
FIG. 4 is a flowchart showing a routine executed by the ECU 30 in the embodiment 1.

FIG. 4 is a flowchart showing a routine executed by the ECU 30 in the embodiment. The routine is started when an ignition switch (IG) is turned on. The routine is repeatedly executed within a certain time, for example, one hour.

In the routine as shown in FIG. 4, it is determined whether or not fuel is supplied (step 100). As described above, the system includes the level sensor 20 for detecting a liquid level of the fuel tank 12. Accordingly, whether or not the fuel is supplied can be determined by the output of the level sensor 20. Specifically, when the difference (=NF−BF) between the output of the level sensor 20 corresponding to a fuel amount (BF) during a previous stop of the vehicle and the output of the level sensor 20 corresponding to a current fuel amount (NF) exceeds, for example, 5 L, it is determined that the fuel is supplied.

When it is determined that the fuel is supplied in step 100, the warning display of the display 24 is turned off (step 110) and then the procedure goes to step 120. On the other hand, when it is determined that the fuel is not supplied in step 100, the procedure directly goes to step 120.

In step 120, an output value A(n) of the dielectric constant sensor 18 is obtained. Subsequently, the output value A(n) is compared with a threshold C (step 130). The threshold C corresponds to the limit value (C) as described in reference to FIG. 2. When the output value A(n) is smaller than the threshold C, the procedure goes to step 140. When the output value A(n) is equal to or larger than the threshold C, the procedure goes to step 150.

In step 140, it is determined whether or not the output value of the dielectric constant sensor 18 is consistently smaller than a previous output value. Specifically, it is determined whether or not the current output value A(n) is smaller than the previous output value A(n−1) and simultaneously the previous output value A(n−1) is smaller than an output value A(n−2) preceding the previous output value. When the output value of the dielectric constant sensor 18 is continuously smaller than the previous output value, it can be determined that the acid ions in the fuel are changing into metallic salts. Accordingly, when the output value of the dielectric constant sensor 18 is continuously smaller than the previous output value, the warning display of the display 24 is turned on. Thus, the driver is encouraged to supply fuel, consume the remaining fuel immediately, extract the remaining fuel to be exchanged with new fuel, or the like. On the other hand, when the output value of the dielectric constant sensor 18 is not consistently smaller than the previous output value, the procedure returns to step 120 to obtain an output value A(n+1) of the dielectric constant sensor 18.

In accordance with the routine shown in FIG. 4 as described above, adverse effects such as metallic corrosion can be prevented because the supply of the fuel containing acid ions to the diesel engine 10 and the like can be avoided. Also, clogging of the fuel supply system or the like caused even when the amount of the acid ions in the fuel is small can be prevented from occurring because the change of acid ions into metallic salts can be detected.

Although the amount of the acid ions is obtained by the dielectric constant sensor 18 in the embodiment, the amount of the acid ions may be detected by other sensors capable of detecting the amount of acid ions or by various methods such as titration. Such other sensors can include a sensor capable of detecting a total acid value and an optical sensor for detecting oxidation depending on an amount of oxygen.

Although it is determined that acid ions in the fuel are changing into metallic salts when the output value of the dielectric constant sensor 18 is smaller than the previous value twice in succession, the number of times required for the determination is not limited to twice. For example, the number of times may be more than twice for improving the determination accuracy or may be less than twice for completing the determination more immediately. Also, the embodiment is not limited to the determination based on the number of times of the output values of the sensor. Any method capable of determining that the amount of the acid ions in the fuel has been reduced during execution of the routine as shown in FIG. 4 can be applicable.

In the embodiment, whether or not the fuel is supplied is determined by the output of the level sensor 20 when the IG is turned on. However, the system also includes the opening/closing sensor 26 of the fuel lid. Therefore, when the IG is turned off, whether or not the fuel is supplied may be simply determined by the output of the opening/closing sensor 26. Further, whether or not the fuel is supplied may be determined by a combination of the output of the opening/closing sensor 26 and the output of the level sensor 20.

The invention claimed is:

1. A fuel degradation detector for an internal combustion engine, comprising:
   fuel supplying means for supplying biomass fuel to the internal combustion engine;
   degradation index obtaining means for regularly obtaining a degradation index indicating a degree of oxidative degradation of the biomass fuel stored in the fuel supplying means;
   decrease ratio obtaining means for obtaining a decrease ratio of the regularly obtained degradation index during a predetermined set period;
   decrease ratio determining means for determining that a metallic salt derived from the biomass fuel has increased in amount when the decrease ratio is higher than a predetermined first threshold; and
   warning means for warning a driver when it is determined that the biomass fuel has degraded or the metallic salt has increased in amount.

2. The fuel degradation detector for an internal combustion engine according to claim 1, further comprising:
   degradation index determining means for determining that the biomass fuel has degraded when the degradation index is higher than a predetermined second threshold,
   wherein the decrease ratio obtaining means obtains the decrease ratio when the degradation index is lower than the second threshold.

3. A fuel degradation detector for an internal combustion engine, comprising:
   a fuel supplying apparatus for supplying biomass fuel to the internal combustion engine;
   a degradation index obtaining apparatus for regularly obtaining a degradation index indicating a degree of oxidative degradation of the biomass fuel stored in the fuel supplying apparatus;
   a decrease ratio obtaining apparatus for obtaining a decrease ratio of the regularly obtained degradation index during a predetermined set period;
   a decrease ratio determining apparatus for determining that a metallic salt derived from the biomass fuel has increased in amount when the decrease ratio is higher than a predetermined first threshold; and
   a warning apparatus for warning a driver when it is determined that the biomass fuel has degraded or the metallic salt has increased in amount.

4. The fuel degradation detector for an internal combustion engine according to claim 1, further comprising:
   a degradation index determining apparatus for determining that the biomass fuel has degraded when the degradation index is higher than a predetermined second threshold,
   wherein the decrease ratio obtaining apparatus obtains the decrease ratio when the degradation index is lower than the second threshold.

* * * * *